United States Patent [19]

Hamilton

[11] 3,940,418

[45] Feb. 24, 1976

[54] ESTERS AND AMIDES OF 4,5-DIHYDROBENZ[G]INDAZOLE-3-CARBOXYLIC ACIDS AND RELATED COMPOUNDS

[75] Inventor: Robert W. Hamilton, Wilmette, Ill.

[73] Assignee: G. D. Searle & Co., Chicago, Ill.

[22] Filed: Apr. 3, 1974

[21] Appl. No.: 457,451

Related U.S. Application Data

[63] Continuation-in-part of Ser. No. 242,232, April 7, 1972, abandoned.

[52] U.S. Cl. 260/310 R; 260/247.2 A; 260/247.2 B; 260/268.7 R; 260/293.6; 260/310 C; 260/310 D; 424/248; 424/250; 424/267; 424/273

[51] Int. Cl.$^2$................ C07D 231/54; A61K 31/415

[58] Field of Search..................... 260/310 R, 310 D

[56] References Cited
OTHER PUBLICATIONS

Auwers et al., Chem. Abst., Vol. 26, p. 4331 (1932).
Boyer et al., Chem. Abst., Vol. 67, No. 53799g (1967).
Fusco et al., Chem. Abst., Vol. 57, column 2209 (1962).
Huisgen et al., Monatsh. Chem., Vol. 98, pp. 1622–1624 relied on (1967).
Ruhemann et al., J. Chem. Soc. (London), Vol. 101, pp. 2542–2543 relied on (1912).
Ruhmann, J. Chem. Soc. (London), Vol. 101, p. 1736 relied on (1912).

*Primary Examiner*—Donald B. Moyer
*Attorney, Agent, or Firm*—John J. Kolano

[57] ABSTRACT

Aminoalkyl esters and amides of 4,5-dihydrobenz[g]indazole-3-carboxylic acids and related compounds are described herein. They are useful as anti-ulcer agents, anti-arrhythmic agents, anti-bacterial agents, anti-protozoal agents, anthelmintics, anti-fungal agents, anti-algal agents and anti-inflammatory agents. The compounds are prepared from the appropriate carboxylic acid, alkyl ester, or acid chloride.

8 Claims, No Drawings

ESTERS AND AMIDES OF 4,5-DIHYDROBENZ[G]INDAZOLE-3-CARBOXYLIC ACIDS AND RELATED COMPOUNDS

The present application is a continuation-in-part of application Ser. No. 242,232, filed Apr. 7, 1972 now abandoned.

The present invention relates to a group of carboxylic acid derivatives which contain the 4,5-dihydro[g]indazole nucleus or a similar nucleus. More particularly, it relates to a group of compounds having the following general formula

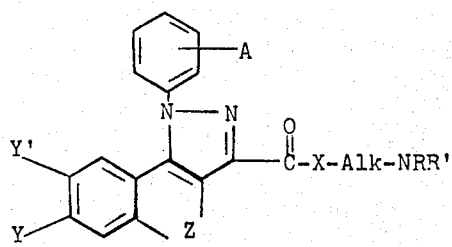

wherein A is selected from the group consisting of hydrogen, halogen, and methoxy; Y is selected from the group consisting of hydrogen, chlorine, methoxy and dimethylamino; Y' is hydrogen or methoxy; Z is methylene, ethylene, trimethylene or vinylene; X is O or —NH—; Alk is lower alkylene separating the atoms attached thereto by at least two carbon atoms; —NRR' is selected from the group consisting of di(lower alkyl)amino, 1-pyrrolidinyl, piperidino, morpholino, 4-methyl-1-piperazinyl and azabicyclononyl. In addition, the present invention encompasses compounds in which the A-substituted phenyl group is replaced by an alkyl group.

The halogen atoms referred to above include fluorine, chlorine, bromine and iodine. The lower alkyl radicals referred to above contain up to 6 carbon atoms and can be exemplified by methyl, ethyl, propyl, isopropyl, and butyl. The lower alkylene radicals referred to above likewise contain up to 6 carbon atoms and can be exemplified by ethylene, propylene and trimethylene.

The organic bases of this invention form pharmaceutically acceptable salts with a variety of organic and inorganic acids. Such salts are formed with acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic, and related acids. They also form quaternary ammonium salts with a variety of organic esters of sulfuric, hydrohalic, and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide, and crotyl bromide.

The compounds of the present invention are conveniently prepared from an acid halide of the formula

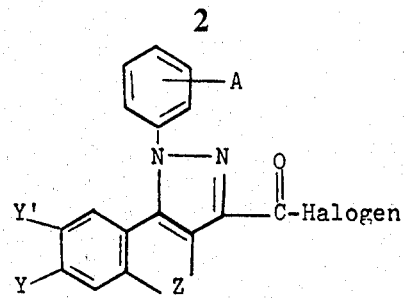

wherein the various groups are defined as above and halogen is preferably chlorine. The acid halide is reacted with an appropriate aminoalkanol or aminoalkylamine to give the desired product.

Alternately, the amides of the present invention can be prepared by reacting a lower alkyl ester, preferably the methyl or ethyl ester corresponding to the acid halide above, with an appropriate aminoalkylamine to give the desired amide. In addition, a carboxylic acid corresponding to the acid chloride depicted above can be heated with an appropriate aminoalkyl halide, preferably the chloride, to give the appropriate aminoalkyl ester.

The compounds of the present invention are useful for a variety of purposes. Thus, they can be used as antiulcer agents, anti-arrhythmic agents, and anti-inflammatory agents. In addition, they are useful as antibiotic agents against a variety of organisms. Thus, they inhibit the growth of bacteria such as *Bacillus subtillus* and *Erwinia* sp.; protozoa such as *Trichomonas vaginalis* and *Tetrahymena pyroformis*; helminths such as *Turbatrix aceti*; fungi such as *Trichophyton mentagrophytes*, *Candida albicans*, and *Verticillium albo-atrum*; and algae such as *Chlorella vulgaris*. For these latter purposes, the present compounds can be combined with various known excipients and adjuvants in the form of dusts, solutions, suspensions, ointments, and sprays to provide compositions useful for disinfecting purposes.

The anti-arrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. Composition of the perfusion solution is the same as Lucchesi's, but the volume is increased to 200 ml. and the temperature lowered to 28°. Aconitine (ordinarily as the nitrate) is administered as soon as the heart beat is regular and EKG pattern normal, the dose being so selected as to at least double the rate. Typically, 0.05 ml of 0.1 percent aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline, is mixed with the perfusion solution. Ten minutes later a like amount is introduced, followed after a further 10 minutes by double the first amount. Final concentration of compound of the perfusion solution is thus 40 mg. per 1. Recording of EKG's is continued at five minute intervals throughout this time and for ten minutes thereafter. A compound is considered antiarrhythmic if, at any time during the 30 minutes immediately following initial administration in at least half of a minimum of two tests, it reduces by 50 percent or more the rate recorded ten minutes after onset of tachycardia. When tested by the above procedure, 7-chloro-N-(3-dimethylaminopropyl)-1-phenyl-4,5-dihydro-1H-benz[g]indazole-3-carboxamide, N-(2-diethylaminoethyl)-1-phenyl-4,5-dihydro-1H-benz[g]indazole-3-carboxamide hydrochloride, 2-diethylaminoethyl 1-(4-chlorophenyl)-4,5-dihydro-1H-benz[g]indazole-3-carboxylate and N-(2-diethylaminoethyl)-1-phenyl-1,4-dihydroindeno[1,2-c]pyrazole-3-carboxamide hydrochloride were each active as anti-arrhythmic agents.

The anti-bacterial utility of the instant compounds is evident from the results of a standardized test for the capacity to prevent the growth of Erwinia sp. In this test, nutrient broth (manufactured by Baltimore Biological Laboratories or Difco) is prepared at twice the concentration recommended by the manufacturer, sterilized, and inoculated with 2 percent (by volume) of a culture of the test organism. Meanwhile, compound is heated in sterile distilled water at a concentration of 2000 γ per ml. and a temperature of 80°C. for 20 min. An equivolume mixture of this compound preparation and the inoculated broth is incubated aerobically at 27°C. for 24–48 hours and then examined grossly for growth of test organism. If growth is observed, the compound is considered inactive. If no such growth is observed, the incubated mixture is serially diluted and mixed with an inoculated broth of the same composition as before excepting that the concentration is halved and 1 percent (by volume) of the culture instead of 2 percent is incorporated. Amounts of the latter broth added are such that concentrations of 100, 10 and 1 γ of compound per ml. result. Mixtures thus obtained are incubated as before and then examined grossly for growth of the test organism. Potency is expressed as the minimum concentration at which no growth of test organism is discernible. Controls are provided by concurrent incubations identical with the foregoing except for the absence of compound. When tested by the above procedure, 7-chloro-N-(2-diethylaminoethyl)-1-phenyl-4,5-dihydro-1H-benz[g]indazole-3-carboxamide hydrochloride, 7-methoxy-N-(2-diethylaminoethyl)-1-(4-chlorophenyl)-4,5-dihydro-1H-benz[g]indazole-3-carboxamide hydrochloride, 7-chloro-N-(2-diethylaminoethyl)-1-phenyl-1H-benz[g]indazole-3-carboxamide hydrochloride, and 3-dimethylaminopropyl 7-chloro-1-phenyl-4,5-dihydro-1H-benz[g]indazole-3-carboxylate each were active at a concentration of 10 micrograms of compound per ml.

The anti-fungal utility of the instant compounds is evident from the results of standardized tests for their capacity to prevent the growth of *Trichophyton mentagrophytes* and *Verticillium albo-atrum* In these tests, two concentrations of Sabouraud dextrose agar (manufactured by Baltimore Biological Laboratories or DIfco) are prepared, one as recommended by the manufacturer and the other at twice this concentration. These preparations are sterilized and then maintained in a fluid state at 80°C. Meanwhile, compound is heated in sterile distilled water at a concentration of 2000 γ per ml. and a temperature of 80°C. for 20 minutes. An equivolume mixture of this compound preparation and the double-strength agar is serially diluted and mixed with the single strength agar in amounts such that concentrations of 1000, 100, 10 and 1 γ of test compound per ml. result. The mixtures thus obtained are allowed to cool and solidify, whereupon they are surface-inoculated with a suspension of T. mentagrophytes or V. albo-atrum and then incubated aerobically at room temperatures. The incubation period is 6–7 days for T. mentagrophytes and 5–7 days for V. albo-atrum. Activity is determined by gross examination, and the potency is expressed as the minimum concentration at which no growth of the test organism is discernible. Controls are provided by concurrent incubations identical with the foregoing except for the absence of compound. When 7-chloro-N-(2-piperidinoethyl)-1-phenyl-4,5-dihydro-1H-benz[g]indazole-3-carboxamide, N-(2-diethylaminoethyl)-1-phenyl-1,4,5,6-tetrahydrobenzo[6,7]cyclohepta[1,2-c]-pyrazole-3-carboxamide maleate, and 2-diethylaminoethyl 7-chloro-1-(4-fluorophenyl)-4,5-dihydro-1H-benz[g]indazole-3carboxylate hydrochloride were tested against Verticillium albo-atrum by the above procedure, each inhibited the growth of the fungus at a concentration of 100 micrograms per ml. or less.

The following examples are presented to further illustrate the present invention; they should not be construed as limiting it in spirit or in scope. In these example, temperatures are indicated in degrees Centigrade (°C.) and quantities are indicated in parts by weight.

EXAMPLE 1

A suspension is prepared from 10 parts of sodium hydride and 70 parts of anhydrous ether and a mixture of, 22 parts of 6-chloro-1-tetralone, 43 parts of dimethyl oxalate and 300 parts of ether is added and the resulting mixture is stirred under nitrogen at 25°C. for 16 hours. The mixture is then decomposed by the addition of 400 parts of water and sufficient aqueous sodium hydroxide solution to make the aqueous layer alkaline. The aqueous layer is then separated and washed three times with ether before it is acidified with concentrated hydrochloric acid. The yellow solid which forms is separated by filtration, washed with water, and dried to give methyl 6-chloro-3,4-dihydro-1-oxo-$\Delta^{2(1H),\alpha}$-naphthaleneglycolate melting at about 92°–93°C.

The above procedure is repeated using 10 parts of sodium hydride, 23 parts of 6-dimethylamino-1-tetralone, and 53 parts of diethyl oxalate and using benzene as the solvent. The mixture is allowed to warm to 45°C. and it is treated with water and base 30 minutes after the addition of the reactants is complete. The crude product is isolated as indicated and then recrystallized from a mixture of benzene and hexane to give ethyl 6-dimethylamino-3,4-dihydro-1-oxo-$\Delta^{2(1H),\alpha}$-naphthaleneglycolate melting at about 91°–92°C.

23 Parts of 5,6-dimethoxy-1-indanone is reacted with 10 parts of sodium hydride and 53 parts of diethyl oxalate according to the procedure described in the first paragraph, using benzene as the solvent. The temperature is maintained between 20° and 30°C. with external cooling and the mixture is stirred for 2 hours and then worked up in the indicated manner. The product obtained is ethyl 5,6-dimethoxy-1-oxo-$\Delta^{2,\alpha}$ indanglycolate melting at about 158°–162°C. 1-Indanone, when reacted in the same way, gives ethyl 1-oxo-$\Delta^{2,\alpha}$-indanglycolate melting at about 69°–70°C.

EXAMPLE 2

A mixture of 20 parts of methyl 6-chloro-3,4-dihydro-1-oxo-$\Delta^{2(1H),}$-naphthaleneglycolate, 12 parts of phenylhydrazine hydrochloride and 150 parts of toluene is heated at reflux with stirring for 6 hours. The water which forms is distilled and removed from the mixture as it is formed. Then, the toluene solvent is distilled off under reduced pressure and the residue is partitioned between chloroform and water. The organic layer is separated, washed twice with water, and then dried over potassium carbonate and the solvent is removed under reduced pressure to leave a residual solid. This is recrystallized from a mixture of benzene and hexane to give methyl 7-chloro-1-phenyl-4,5-dihydro-1H-benz[g]indazole -3-carboxylate melting at about 190°–192°C.

If the above procedure is repeated using the appropriate starting materials, the following compounds are obtained:

Methyl 7-chloro-1-(4-fluorophenyl)-4,5-dihydro-1H-benz[g]indazole-3-carboxylate melting at about 169°–171°C. after recrystallization from methanol.

Methyl 7-chloro-1-(4-methoxyphenyl)-4,5-dihydro-1H-benz[g]indazole-3-carboxylate melting at about 177°–181°C. after recrystallization from methanol.

Methyl 1-(4-chlorophenyl)-4,5-dihydro-1H-benz[g]indazole-3-carboxylate melting at about 198°–199°C. after recrystallization from a mixture of benzene and hexane.

Methyl 1-(4-chlorophenyl)-7-methoxy-4,5-dihydro-1H-benz[g]indazole-3-carboxylate melting at about 187.5–189°C. after recrystallization from a mixture of benzene and hexane.

Ethyl 7-dimethylamino-1-phenyl-4,5-dihydro-1H-benz[g]indazole-3-carboxylate melting at about 172.5°14 174°C.

Ethyl 1-isopropyl-4,5-dihydro-1H-benz[g]indazole-3-carboxylate melting at about 102°–104°C. after recrystallization from hexane.

Ethyl 1-phenyl-1,4-dihydroindeno[1,2-c]pyrazole-3-carboxylate melting at about 112°–114°C.

Ethyl 6,7-dimethoxy-1-phenyl-1,4-dihydroindeno[1,2-c]pyrazole-3-carboxylate melting at about 171°–172.5°C. after recrystallization from a mixture of benzene and hexane.

EXAMPLE 3

A mixture of 25 parts of 5,6-dihydro-4H-benzo[6,7]cyclohepta[1,2-b]furan-2,3-dione, 21 parts of phenylhydrazine hydrochloride and 400 parts of absolute ethanol are refluxed for 6 hours. The ethanol is then removed under reduced pressure and the resulting residue is partitioned between benzene and water with sufficient potassium carbonate being added to make the mixture alkaline. The organic layer is then separated and washed twice with water before it is dried over potassium carbonate and the solvent is evaporated under reduced pressure. The resulting residue is recrystallized from hexane to give ethyl 1-phenyl-1,4,5,6-tetrahydrobenzo-[6,7]cyclohepta[1,2-c]pyrazole-3-carboxylate melting at about 110°–111°C.

EXAMPLE 4

A mixture of 15 parts of methyl 7-chloro-1-phenyl-4,5-dihydro-1H-benz[g]indazole-3-carboxylate and 19 parts of 2,3-dichloro-5,6-dicyano-1,4-benzoquinone in 150 parts of dioxane is heated at reflux for 20 hours. The mixture is then cooled to 25°C. and filtered. The solvent is evaporated from the filtrate at reduced pressure and the residue is partitioned between benzene and water with sufficient aqueous sodium hydroxide added to make the mixture just alkaline. The benzene layer is then separated, washed twice with water and the benzene is distilled off under reduced pressure. The resulting residue, which is methyl 7-chloro-1-phenyl-1H-benz[g]-indazole-3-carboxylate, showed complete aromatization in a NMR spectrum.

EXAMPLE 5

A mixture of 15 parts of methyl 7-chloro-1-phenyl-4,5-dihydro-1H-benz[g]indazole-3-carboxylate, 100 parts of aqueous 10 percent sodium hydroxide solution and 120 parts of methanol is refluxed and stirred for 3 hours. The mixture is then cooled and acidified with concentrated hydrochloric acid. The solid which forms is separated by filtration, washed with water, and dried to give 7-chloro-1-phenyl-4,5-dihydro-1H-benz[g]indazole-3-carboxylic acid melting at about 282°C. with evolution of gas.

If the above procedure is repeated using the appropriate starting materials, the following compounds are obtained:

7-Chloro-1-(4-fluorophenyl)-4,5-dihydro-1H-benz[g]indazole-3-carboxylic acid.

7-Chloro-1-(4-methoxyphenyl)-4,5-dihydro-1H-benz[g]indazole-3-carboxylic acid.

1-(4-Chlorophenyl)-4,5-dihydro-1H-benz[g]indazole-3-carboxylic acid melting at about 270°C. with evolution of gas after recrystallization from methylene chloride.

1-(4-Chlorophenyl)-7-methoxy-4,5-dihydro-1H-benz[g]indazole-3-carboxylic acid melting at about 227°–228°C. with gas evolution after recrystallization from ethanol.

1-Phenyl-1,4,5,6-tetrahydrobenzo[6,7]cyclohepta[1,2-c]pyrazole-3-carboxylic acid melting at about 196°–199°C. after recrystallization from a mixture of benzene and hexane.

7-Chloro-1-phenyl-1H-benz[g]indazole-3-carboxylic acid melting at about 287°–289°C. with evolution of gas after recrystallization from a mixture of dimethyl sulfoxide and water.

1-Isopropyl-4,5-dihydro-1H-benz[g]indazole-3-carboxylic acid melting at about 193.5°–195.5°C.

1-Phenyl-1,4-dihydroindeno[1,2-c]pyrazole-3-carboxylic acid melting at about 250°C. with evolution of gas.

EXAMPLE 6

A mixture of 5 parts of methyl 7-chloro-1-phenyl-4,5-dihydro-1H-benz[g]indazole-3-carboxylate and 40 parts of 2-diethylaminoethylamine is heated at reflux for 3 hours. Excess amine is distilled off under reduced pressure and the reside is partitioned in ether and dilute aqueous hydrochloric acid. The aqueous layer is then separated and washed twice with ether and it is made alkaline with an aqueous sodium hydroxide solution. The resulting mixture is then extracted with ether and the ether extracts are dried over potassium carbonate. The ether solvent is removed under reduced pressure, the resulting oil is dissolved in anhydrous ethanol, and a slight excess of hydrogen chloride in 2-propanol is added. Anhydrous ether is then added until the mixture becomes turbid, and the mixture is cooled. The solid which forms is separated by filtration and recrystallized from a mixture of ethanol and ether to give 7-chloro-N-(2-diethylaminoethyl)-1-phenyl-4,5-dihydro-1H-benz[g]indazole-3-carboxamide hydrochloride melting at about 229°–231°C. The free base of this compound has the following formula

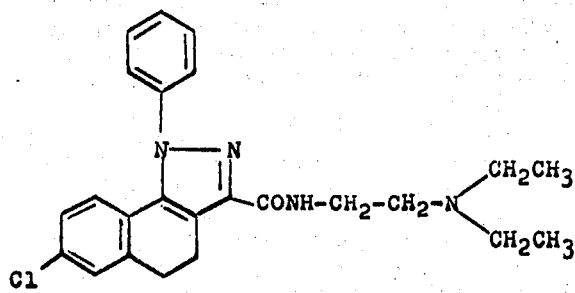

EXAMPLE 7

A mixture of 6 parts of 7-chloro-N-(2-diethyl-aminoethyl)-1-phenyl-4,5-dihydro-1H-benz[g]indazole-3-carboxamide hydrochloride and 6 parts of methyl iodide in 150 parts of chloroform is heated at 60°C. in a citrate bottle for 16 hours. The chloroform is then distilled off under reduced pressure and the reside is dissolved in anhydrous ethanol. Anhydrous ether is added to the point of turbidity and the mixture is cooled. The crystals which form are separated by filtration to give 7-chloro-N-(2-diethylaminoethyl)-1-phenyl-4,5-dihydro-1H-benz[g]indazole-3-carboxamide methiodide melting at about 244°–245°C. with evolution of gas.

EXAMPLE 8

If the procedure of Example 6 is repeated using the appropriate amine in place of the 2-diethylaminoethylamine, the following compounds are obtained:

7-Chloro-N-(3-dimethylaminopropyl)-1-phenyl-4,5-dihydro-1H-benz[g]indazole-3-carboxamide melting at about 98°–99°C. after recrystallization from a mixture of benzene and hexane.

7-Chloro-N-(2-diisopropylaminoethyl)-1-phenyl-4,5-dihydro-1H-benz[g]indazole-3-carboxamide as the hydrochloride salt containing 1 equivalent of ethanol. This material melts at about 218°–225°C.

7-Chloro-N-(2-piperidinoethyl)-1-phenyl-4,5-dihydro-1H-benz[g]indazole-3-carboxamide melting at about 116.5°–118°C. after recrystallization from a mixture of benzene and hexane.

7-Chloro-N-[2-(1-pyrrolidinyl)ethyl]-1-phenyl-4,5,-dihydro-1H-benz[g]indazole-3-carboxamide melting at about 121°–124°C. after recrystallization from a mixture of benzene and hexane.

EXAMPLE 9

5 Part of ethyl 7-dimethylamino-1-phenyl-4,5-dihydro-1H-benz[g]indazole-3-carboxylate is reacted with 2-diethylaminoethylamine according to the procedure described in Example 6. The product obtained is 7-dimethylamino-N-(2-diethylaminoethyl)-1-phenyl-4,5-dihydro-1H-benz[g]indazole-3-carboxamide dihydrochloride melting at about 230°–236°C. with evolution of gas.

Similarly, if 5 parts of ethyl 1-phenyl-1,4-dihydroindeno[1,2-c]pyrazole-3-carboxylate is reacted with 2diethylaminoethylamine, the product obtained is N-(2-diethylaminoethyl)-1-phenyl-1,4-dihydroindeno[1,2-c]-pyrazole-3-carboxamide hydrochloride melting at about 179°–181°C. The free base of this compound has the following formula

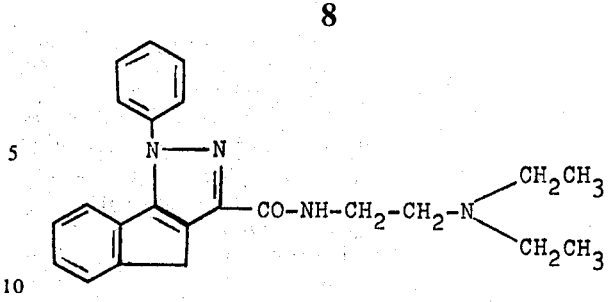

Likewise, ethyl 6,7-dimethoxy-1-phenyl-1,4-dihydroindeno[1,2-c]pyrazole-3-carboxylate is reacted with 2-diethylaminoethylamine to first give an oil which is 6,7-dimethoxy-N-(2-diethylaminoethyl)-1-phenyl-1,4-dihydroindeno[1,2-c]pyrazole-3-carboxamide and then to give 6,7-dimethoxy-N-(2-diethylaminoethyl)-1-phenyl-1,4-dihydroindeno[1,2-c]pyrazole-3-carboxamide hydrochloride melting at about 245°–246°C. with evolution of gas.

EXAMPLE 10

A mixture of 5 parts of 7-chloro-1-phenyl-4,5-dihydro-1H-benz[g]indazole-3-carboxylic acid and 50 parts of thionyl chloride is heated on a steam bath until evolution of sulfur dioxide ceases. The excess thionyl chloride is then removed under reduced pressure and 50 parts of benzene is added to the resulting residue. The benzene is then distilled off under reduced pressure and the new residue is dissolved in 50 parts of benzene and 5 parts 2-diethylaminoethanol is added with stirring. The mixture is allowed to become warm and it is allowed to stand for 1 hour. Excess 2-diethylaminoethanol is distilled off under reduced pressure and the residue is partitioned with dilute hydrochloric acid and ether. The aqueous layer is separated and washed twice with ether before it is made alkaline with dilute sodium hydroxide and extracted with ether. The resulting ether solution is dried over potassium carbonate and concentrated. The residue obtained is 2-diethylaminoethyl 7-chloro-1-phenyl-4,5-dihydro-1H-benz[g]indazole-3-carboxylate. It is dissolved in anhydrous ethanol and a slight excess of hydrogen chloride in 2-propanol is added. Anhydrous ether is then added until the mixture becomes tubid and it is then cooled. The crystals which form are separated by filtration and recrystallized from a mixture of anhydrous ethanol and anhydrous ether to give 2-diethylaminoethyl 7-chloro-1-phenyl-4,5-dihydro-1H-benz[g]indazole-3-carboxylate hydrochloride melting at about 190°–192°C. The free base of this compound has the following formula

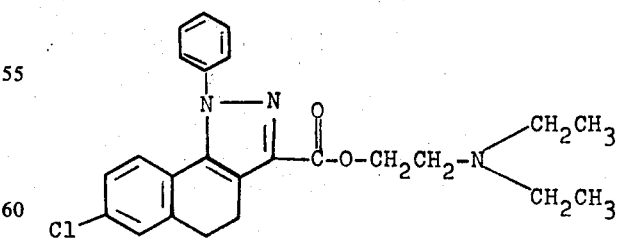

EXAMPLE 11

6 Parts of 3-(2-aminoethyl)-3-azabicyclo[3.2.2]-nonane is substituted for the 5 parts of 2-diethylaminoethanol and the procedure of Example 10 is repeated. The product obtained is 7-chloro-N-[2-(3-azabicyclo[3.2.2]non-3-yl)ethyl]-1-phenyl-4,5-dihydro-1H-benz[g]indazole-3-carboxamide hydrochloride hemihydrate melting at about 246°–249°C.

EXAMPLE 12

If the procedure of Example 10 is repeated using the appropriate carboxylic acid and aminoalkanol, the following compounds are obtained:

3-Dimethylaminopropyl 7-chloro-1-phenyl-4,5-dihydro-1H-benz[g]indazole-3-carboxylate melting at about 111°–112°C. after recrystallization from a mixture of benzene and hexane.

2-Diethylaminoethyl 7-chloro-1-(4-fluorophenyl)-4,5-dihydro-1H-benz[g]indazole-3-carboxylate hydrochloride melting at about 202°–204°C.

2-Diethylaminoethyl 1-phenyl-4,5-dihydro-1H-benz[g]indazole-3-carboxylate as the hydrochloride salt melting at about 179°–181°C.

2-Diethylaminoethyl 1-phenyl-1,4,5,6-tetrahydrobenzo[6,7]cyclohepta[1,2-c]pyrazole-3-carboxylate. In this case the free base is dissolved in 40 parts of anhydrous ethanol and 2.3 parts of maleic acid in 40 parts of anhydrous ethanol is added. Then, anhydrous ether is added to the point of turbidity. The mixture is cooled and the crystals which form are separated. This is the monomaleate salt and it melts at about 127°–129°C.

2-Diethylaminoethyl 1-phenyl-1,4-dihydroindeno[1,2-c]pyrazole-3-carboxylate.

EXAMPLE 13

If the procedure of Example 10 is repeated using the appropriate carboxylic acid and aminoalkylamine, the following compounds are obtained:

7-Chloro-N-(2-dimethylaminoethyl)-1-phenyl-4,5-dihydro-1H-benz[g]indazole-3-carboxamide melting at about 161.5°–162.5°C. after recrystallization of the crude free amine from a mixture of benzene and hexane.

7-Chloro-N-(2-diethylaminoethyl)-1-(4-fluorophenyl)-4,5-dihydro-1H-benz[g]indazole-3-carboxamide melting at about 109°–110°C. after recrystallization of the crude free amine from a mixture of benzene and hexane.

7-Chloro-N-(2-diethylaminoethyl)-1-(4-methoxyphenyl)-4,5-dihydro-1H-benz[g]indazole -3-carboxamide melting at about 121°–123°C. after recrystallization of the crude free amine from a mixture of benzene and hexane.

7-Chloro-N-(3-piperidinopropyl)-1-phenyl-4,5-dihydro-1H-benz[g]indazole-3-carboxamide melting at about 141.5°–142.5°C. after recrystallization of the crude free amine from a mixture of benzene and hexane.

7-Chloro-N-(2-morpholinoethyl)-1-phenyl-4,5-dihydro-1H-benz[g]indazole-3-carboxamide melting at about 125°–127°C. after recrystallization of the crude free amine from a mixture of benzene and hexane.

N-(2-Diethylaminoethyl)-1-phenyl-4,5-dihydro-1H-benz[g]indazole-3-carboxamide hydrochloride melting at about 178°–180°C. This hydrochloride is obtained via the free base, N-(2-diethylaminoethyl)-1-phenyl-4,5-dihydro-1H-benz[g]indazole-3-carboxamide, as described in the procedure of Example 10.

N-(2-Diethylaminoethyl)-1-(4-chlorophenyl)-4,5-dihydro-1H-benz[g]indazole-3-carboxamide hydrochloride melting at about 220°–221°C. after recrystallization from a mixture of anhydrous ethanol and anhydrous ether.

7-Methoxy-N-(2-diethylaminoethyl)-1-(4-chlorophenyl)-4,5-dihydro-1H-benz[g]indazole-3-carboxamide hydrochloride melting at about 241°–242°C. after recrystallization from an anhydrous mixture of ethanol and ether.

7-Methoxy-N-(3-dimethylaminopropyl)-1-(4-chlorophenyl)-4,5-dihydro-1H-benz[g]indazole-3-carboxamide hydrochloride melting at about 255.5°–256°C. after recrystallization from an anhydrous mixture of ethanol and ether.

7-Chloro-N-(2-diethylaminoethyl)-1-phenyl-1H-benz[g]indazole-3-carboxamide hydrochloride melting at about 216°–219°C. after recrystallization from aqueous ethanol.

N-(2-Morpholinoethyl)-1-pheny-1,4-dihydroindeno[1,2-c]pyrazole-3-carboxamide melting at about 130°–131°C. after recrystallization from a mixture of benzene and hexane.

N-(2-Diethylaminoethyl)-1-phenyl-1,4,5,6-tetrahydrobenzo[6,7]cyclohepta[1,2-c]pyrazole-3-carboxamide as the monomaleate salt melting at about 173°–174°C.

N-(2-Diethylaminoethyl)-1-isopropyl-4,5-dihydro-1H-benz[g]indazole-3-carboxamide melting at about 131–134°C. after recrystallization from an anhydrous mixture of ethanol and ether.

7-Chloro-N-[2-(4-methyl-1-piperazinyl)ethyl]-1-phenyl-4,5-dihydro-1H-benz[g]indazole-3-carboxamide.

EXAMPLE 14

A mixture of 10 parts of 1-(4-chlorophenyl)-4,5-dihydro-1H-benz[g]indazole-3-carboxylic acid, 5parts of 2-diethylaminoethyl chloride and 160 parts of anhydrous 2-propanol is heated at reflux for 16 hours. The 2-propanol is then removed under reduced pressure and the resulting residue is partitioned in ether and dilute hydrochloric acid. The aqueous layer is separated and washed twice with ether. It is then made alkaline with cold aqueous sodium hydroxide solution and then extracted with ether. The combined ether extracts are dried over potassium carbonate and the solvent is evaporated to leave a residual free base. This is recrystallized from a mixture of benzene and hexane to give 2-diethylaminoethyl 1-(4-chlorophenyl)-4,5-dihydro-1H-benz[g]indazole-3-carboxylate melting at about 102°–103°C.

If the above procedure is repeated using the appropriate carboxylic acid and aminoalkyl chloride as the starting materials, the following compounds are obtained:

2-Diethylaminoethyl 7-chloro-1-(4-methoxyphenyl)-4,5-dihydro-1H-benz[g]indazole-3-carboxylate.

2-Diethylaminoethyl 7-methoxy-1-(4-chlorophenyl)-4,5-dihydro-1H-benz[g]indazole-3-carboxylate.

2-Diethylaminoethyl 7-chloro-1-phenyl-1H-benz[g]indazole-3-carboxylate.

2-(1-Pyrrolidinyl)ethyl 7-chloro-1-phenyl-4,5-dihydro-1H-benz[g]indazole-3-carboxylate.

2-Piperidinoethyl 7-chloro-1-phenyl-4,5dihydro-1H-benz[g]indazole-3-carboxylate.

2-Morpholinoethyl 7-chloro-1-phenyl-4,5-dihydro-1H-benz[g]indazole-3-carboxylate.

2-(4methyl-1-piperazinyl)ethyl 7-chloro-1-phenyl-4,5-dihydro-1H-benz[g]indazole-3-carboxylate.

What is claimed is:

1. A compound of the formula

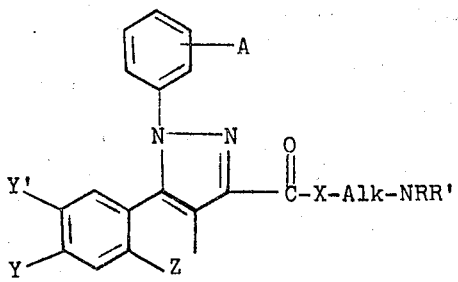

wherein A is selected from the group consisting of hydrogen, halogen, and methoxy; Y is selected from the group consisting of hydrogen, chlorine, and methoxy; Y' is hydrogen or methoxy; Z is methylene, ethylene, trimethylene, or vinylene; X is O or —NH—; Alk is lower alkylene containing up to 6 carbon atoms and separating the atoms attached thereto by at least two carbon atoms; NRR' is selected from the group consisting of di(lower alkyl)-amino wherein each lower alkyl group contains up to 6 carbon atoms, 1-pyrrolidinyl, and piperidino.

2. A compound according to claim 1 which has the formula

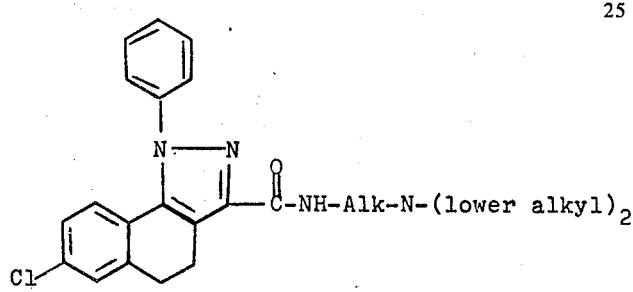

wherein Alk is lower alkylene containing up to 6 carbon atoms and separating the atoms attached thereto by at least two carbon atoms and the lower alkyl groups each contain up to 6 carbon atoms.

3. A compound according to claim 1 which is 7-chloro-N-(2-diethylaminoethyl)-1-phenyl-4,5-dihydro-1H-benz[g]indazole-3-carboxamide.

4. A compound according to claim 2 which is 7-chloro-N-(3-dimethylaminopropyl)-1-phenyl-4,5-dihydro-1H-benz[g]indazole-3-carboxamide.

5. A compound according to claim 2 which is N-(2-diethylaminoethyl)-1-phenyl-4,5-dihydro-1H-benz[g]indazole-3-carboxamide.

6. A compound according to claim 2 which is 6,7-dimethoxy-N-(2-diethylaminoethyl)-1-phenyl-1,4-dihydroindeno[1,2,-c]pyrazole-3-carboxamide.

7. A compound according to claim 2 which is 3-dimethylaminopropyl 7-chloro-1-phenyl-4,5-dihydro-1H-benz[g]indazole-3-carboxylate.

8. A compound according to claim 2 which is 2-diethylaminoethyl 1-(4-chlorophenyl)-4,5-dihydro-1H-benz[g]indazole-3-carboxylate.

* * * * *

UNITED STATES PATENT OFFICE
CERTIFICATE OF CORRECTION

PATENT NO. : 3,940,418
DATED : February 24, 1976
INVENTOR(S) : Robert W. Hamilton It is certified that error appears in the above-identified patent and that said Letters Patent are hereby corrected as shown below:

Column 4, line 68 -- "$\Delta^{2(1H)},$" should read -- $\Delta^{2(1H),\alpha}$ --.

Column 5, line 33 -- "172.5°14 174°C" should read -- 172.5°-174°C. --.

Column 7, line 64 -- "2 diethylaminoethylamine" should read -- 2-diethylaminoethylamine --.

Column 8, line 45 -- "tubid" should read -- turbid --.

Signed and Sealed this

*fifteenth* Day of *June 1976*

[SEAL]

Attest:

RUTH C. MASON
*Attesting Officer*

C. MARSHALL DANN
*Commissioner of Patents and Trademarks*